United States Patent [19]

Honda et al.

[11] Patent Number: 4,822,892

[45] Date of Patent: Apr. 18, 1989

[54] N-HETEROCYCLIC PLATINUM COMPLEXES

[75] Inventors: Masamitsu Honda; Kazumi Morikawa; Kohichi Endoh, all of Tokyo, Japan

[73] Assignee: Chugai Seiyaku Kabushiki Kaisha, Tokyo, Japan

[21] Appl. No.: 165,404

[22] Filed: Feb. 24, 1988

Related U.S. Application Data

[63] Continuation of Ser. No. 770,671, Aug. 29, 1985, abandoned.

[30] Foreign Application Priority Data

| Sep. 12, 1984 | [JP] | Japan | 59-189655 |
| Sep. 12, 1984 | [JP] | Japan | 59-189656 |
| Sep. 12, 1984 | [JP] | Japan | 59-189657 |
| Dec. 22, 1984 | [JP] | Japan | 59-271411 |
| Jan. 22, 1985 | [JP] | Japan | 60-8383 |
| Apr. 25, 1985 | [JP] | Japan | 60-87615 |
| Apr. 25, 1985 | [JP] | Japan | 60-87616 |
| Aug. 1, 1985 | [JP] | Japan | 60-168559 |
| Aug. 1, 1985 | [JP] | Japan | 60-168560 |

[51] Int. Cl.$^4$ .................. A61K 31/555; C07F 15/00
[52] U.S. Cl. .................. 548/402; 548/950; 548/955
[58] Field of Search .................. 548/402, 950, 955; 514/184

[56] References Cited

U.S. PATENT DOCUMENTS

| 4,170,591 | 10/1979 | Motes | 548/955 |
| 4,410,544 | 10/1983 | Berg et al. | 556/137 X |
| 4,431,666 | 2/1984 | Bulten et al. | 556/137 X |
| 4,466,924 | 8/1984 | Verbeek et al. | 556/137 |
| 4,584,316 | 3/1986 | Rosenberg et al. | 514/492 |
| 4,607,114 | 8/1986 | Nakayama et al. | 556/137 |

FOREIGN PATENT DOCUMENTS

| 0115929 | 8/1984 | European Pat. Off. |
| 0176005 | 4/1986 | European Pat. Off. |
| 2182941 | 12/1973 | France |
| 2128615 | 5/1984 | United Kingdom |

OTHER PUBLICATIONS

Simon et al., Rev. Roum. Biochem., vol. 14, No. 2, pp. 117-125 (1977).
Inagaki et al., Inorganica Chimica Acta, vol. 37, pp. L547-L548 (1979).
Hacker et al., Proc. of the Am. Assoc. of Cancer Research Abstracts, Abstract 652, p. 166 (1982).
Tanabe Seiyaku KK, Derwent Abstract 84-131256/21 of Japan 67,262 (04/16/84).
Chugai Pharm KK, Derwent Abstract 85-240374/39 of Japan 158,195, (08/19/85).
Simon et al., Chemical Abstracts, vol. 87, 145547q (1977).
Bystrenina et al., Chemical Abstracts, vol. 96, 85741x (1982).
Minacheva et al., Chemical Abstracts, vol. 100, No. 26, 220,572m (06/25/84).
Bystrenina et al., Chemical Abstracts, vol. 103, No. 4, 31594w, (07/29/85).
Inagaki et al., "Synthesis and Anti-Tumor Activity of Amino-Methylpiperidine Platinum (II) Complexes", Chem. Abstr., vol. 93, 1980, 36830e.
Sosnovsky et al., "In the Search for New Anticancer Drugs. VII. Platinum Complexes of Diaziridines and Azetidine", Chem. Abstr., vol. 101, 1984, 143678s.

Primary Examiner—Donald G. Daus
Assistant Examiner—Diana G. Rivers
Attorney, Agent, or Firm—Browdy & Neimark

[57] ABSTRACT

Novel platinum complexes represented by the formula:

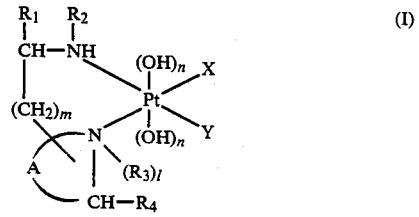

wherein A is alkylene having carbon atoms of from 1 to 3; $R_1$, $R_2$, $R_3$ and $R_4$ are the same or different and are hydrogen or alkyl having carbon atoms of from 1 to 4; X and Y are independently a halogen atom, or combined together to form

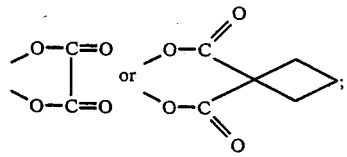

and l, m and n are independently 0 or 1, and a process for preparing the same are disclosed.

These platinum complexes have high antitumor activity and low toxicity, and are easily soluble in water. Therefore, they are very useful as an antitumor agent.

5 Claims, No Drawings

N-HETEROCYCLIC PLATINUM COMPLEXES

This application is a continuation of application Ser. No. 770,671, filed Aug. 29, 1985, now abandoned.

FIELD OF THE INVENTION

This invention relates to a novel platinum complex represented by the formula (I):

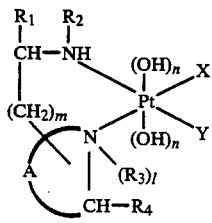
(I)

wherein A is alkylene having carbon atoms of from 1 to 3; $R_1$, $R_2$, $R_3$ and $R_4$ are the same or different and are hydrogen or alkyl having carbon atoms of from 1 to 4; X and Y are independently a halogen atom or combined together to form

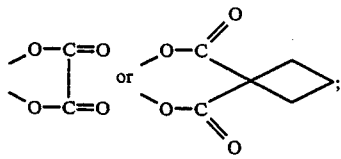

and l, m and n are independently 0 or 1.

This complex is useful as an antitumor agent.

BACKGROUND OF THE INVENTION

Since Rosenberg et al reported that cisplatin (abbreviated as CDDP hereunder) has antitumor activity (Nature 222, 385 (1969)), many researchers have eagerly investigated to seek platinum complexes with a view of finding ones having antitumor activities. For example, some of these compounds appear in Japanese Patent Publication No. 5599/84, Japanese Patent Public Disclosure No. 77694/82, etc.

Although the known platinum complexes including CDDP were recognized to exhibit a broad spectrum of antitumor activities, their dosage amounts and the sorts of tumors which could be treated were limited because these complexes have very serious nephrotoxicity. In addition, it is observed that these platinum complexes generally bind to plasma proteins so as to be converted into an inactivated form.

The inventors of this invention have studied various platinum complexes in order to identify those having high antitumor activities and less toxicity. Finally, we found the compounds of this invention and confirmed that these complexes are suitable for use as an antitumor agent.

The compounds of this invention are prepared by the following method.

Platinum(II)potassium chloride is reacted with a diamine derivative represented by the formula (II):

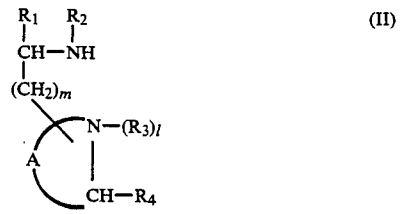
(II)

wherein A, $R_1$, $R_2$, $R_3$, $R_4$, l and m are the same as defined above to give the corresponding dichloro compound [formula (I) (n is 0, X and Y are chlorine)]. The resulting dichloro compound is oxidized with hydrogen peroxide to give a novel platinum complex of the formula (I) [n=1, X=Y=Cl] defined above. The dichloro compound is converted to dinitrate form with use of silver nitrate, and then reacted with a dicarboxylic acid to give a novel platinum complex of the formula (I) [n is 0, X and Y are

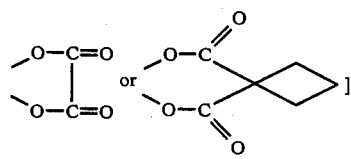
]

defined above.

Diamine derivatives which can be used in this invention include 2-aminomethylpyrrolidine, (S)-2-aminomethylpyrrolidine, (R)-2-aminomethylpyrrolidine, 2-(1-aminoethyl)pyrrolidine, 2-aminomethyl-1-methylpyrrolidine, 2-aminomethyl-1-ethylpyrrolidine, 2-aminomethyl-1,5-dimethylpyrrolidine, 1-(2-aminoethyl)pyrrolidine, 2-aminoethylazetidne, 2-aminomethylaziridine, and the like.

Dicarboxylic acids which are useful in this invention include oxalic acid, 1,1-cyclobutanedicarboxylic acid and their salts.

The platinum complex of this invention can be formulated by any desirable conventional method with a pharmaceutically acceptable carrier and, if necessary, an adjuvant.

For oral administration, the compound of this invention can be formulated into a solid preparation such as tablets, pills, granules, powder, capsules, or the like, or a liquid preparation such as solution, suspension, emulsion or the like. When the preparation is used for parenteral administration, the preparation is formulated into a suppository, injection, an intravenous drip infusion or the like. When the compound of this invention is formulated into tablets, pills, granules, powder or capsules, pharmaceutical carriers such as starch, sucrose, crystalline cellulose, kaolin, calcium carbonate, talc, magnesium carbonate and the like are preferably used. For preparation of an injection, it is preferred that the compound is dissolved in distilled water or an aqueous solution of a salt such as sodium chloride. For preparation of an intravenous drip infusion, the compound is dissolved in a suitable fluid therapy such as a physiological saline, a glucose-sodium chloride solution or the like. For the suppository, cacao butter, laurin, glycerogelatin, macrogol are preferably used as a base.

The amount of the compound in a formulated preparation is selected so as to be appropriately administered depending on the age and condition of individual patient being treated.

The compound of this invention is preferably administrated orally in a daily dose of from 200 to 400 mg/m$^2$, and parenterally in a daily dose of from 100 to 200 mg/m$^2$.

The compound of this invention has very low toxicity. For example, when ddY strain male mouse (5 week old, weighing 26–30 g) was intraperitoneally administered, the compound of this invention as an aqueous solution, the LD$_{50}$ was higher than 80 mg/kg.

As described above, since the compound of this invention has high antitumor activity and low toxicity, and is easily soluble in water, it is very useful as a drug.

This invention is further illustrated in the following Examples and Experiments, but they should not be interpreted as limitative of this invention.

EXAMPLE 1

To a solution of platinum(II) potassium chloride (4.15 g:0.01 mole) in 100 ml of water was added a solution of 2-aminomethylpyrrolidine (1.00 g:0.01 mole) in 10 ml of water. The mixture was stirred at room temperature for 1 day. The resulting solid was collected by filtration, washed with water, and dried at 60° C. under reduced pressure for 3 hours to give 3.00 g of dichloro-(2-aminomethylpyrrolidine)platinum(II). Yield: 82%, m.p. 255°–270° C. (decomposition).

Analysis: Calcd. for C$_5$H$_{12}$Cl$_2$N$_2$Pt: C 16.39, H 3.30, N 7.65 (%). Found: C 16.40, H 3.26, N 7.50 (%).

IR spectrum: $\nu_{max}^{KBr}$ cm$^{-1}$: 3420, 3230, 3170 (>NH)

To a suspension of the product obtained above (3.00 g:0.0082 mole) in 300 ml of water was added silver nitrate (2.78 g:0.0164 mole). The mixture was stirred at room temperature under light shielding for 3 days. The resulting white precipitate of silver chloride was removed by filtration using a millipore filter (0.22 μm). The filtrate, which contained the unreacted silver nitrate, was treated with a sodium chloride aqueous solution. The resulting silver chloride was removed by filtration, and the filtrate was evaporated at a temperature below 40° C. under reduced pressure into 60 ml. To the above solution was added disodium 1,1-cyclobutanedicarboxylate (1.54 g:0.0082 mole) with stirring, and the mixture was subjected to reaction at room temperature for 4 days.

The resulting white crystalline solid was recovered by filtration, washed with water, and dried at 60° C. under reduced pressure for 3 hours to give as dried product 1.86 g of 1,1-cyclobutanedicarboxylate(2-aminomethylpyrrolidine)platinum(II). Yield: 52%, m.p. 235°–255° C. (decomposition).

Analysis: Calcd. for C$_{11}$H$_{18}$N$_2$O$_4$Pt: C 30.20, H 4.15, N 6.40 (%). Found: C 30.00, H 4.11, N 6.61 (%).

IR Spectrum: $\nu_{max}^{KBr}$ cm$^{-1}$: 3080 (>NH), 1640, 1660 (>C=O)

The obtained dried product was recrystallized from water to give, as the purified product, 1.61 g of 1,1-cyclobutanedicarboxylate(2-aminomethylpyrrolidine)platinum(II) (compound 1). Total yield: 45%, m.p. 215°–220° C. (decomposition).

Analysis: Calcd. for C$_{11}$H$_{18}$N$_2$O$_4$Pt: C 30.20, H 4.15, N 6.40 (%). Found: C 30.02, H 4.13, N 6.43 (%).

IR spectrum: $\nu_{max}^{KBr}$ cm$^{-1}$: 3100, 3190 (>NH), 1590, 1635 (>C=O)

EXAMPLE 2

To a solution of (S)-proline (25 g:0.22 mole) and sodium hydroxide (8.7 g:0.22 mole) in 150 ml of water was slowly added a solution of benzylchloroformate (43.5 g:0.26 mole) and sodium hydroxide (11.6 g:0.29 mole) in 75 ml of water with stirring under cooling on ice over 30 minutes, followed by continuing the stirring at the same temperature for 15 minutes. From the reaction mixture, excess benzylchloroformate was removed by extraction with 150 ml of chloroform. The aqueous layer was acidified with 5N hydrochloric acid, and the resulting oily product was extracted with chloroform. After drying the chloroform layer over magnesium sulfate, chloroform was removed by evaporation to give 52.2 g of (S)-1-carbobenzoxypyrrolidine-2-carboxylic acid as oil. Yield: 96%.

To a solution of the resulting (S)-1-carbobenzoxypyrrolidine-2-carboxylic acid (52.2 g:0.21 mole) and triethylamine (21.2 g:0.21 mole) in 525 ml of chloroform was added isobutyl chloroformate (28.7 g:0.21 mole) with stirring under cooling on ice, followed by continuing the stirring for 15 minutes. Dried ammonia gas was bubbled into the mixture for 1 hour and then the mixture was allowed to warm to room temperature and stand overnight. The resulting white precipitate was removed by the filtration, and the filtrate was evaporated under reduced pressure. The residue was dissolved in 200 ml of chloroform and was washed with diluted aqueous hydrochloric acid and water, and dried over magnesium sulfate. Chloroform was distilled off to give 45.8 g of (S)-1-carbobenzoxypyrrolidine-2-carboxamide. Yield: 88%.

(S)-1-carbobenzoxypyrrolidine-2-carboxamide (45.8 g:0.18 mole) was dissolved in 400 ml of absolute methanol and catalytically reduced in a usual manner by addition of 10 g of 10% palladium on charcoal under a hydrogen gas steam. After completion of the reaction, the catalyst was removed and then the solvent was distilled off under reduced pressure. The residue was crystallized from n-hexane and benzene, and washed with n-hexane to give 18.8 g of (S)-pyrrolidine-2-carboxamide as white solid. Yield: 89%, m.p. 85°–90° C.

To a solution of (S)-pyrrolidine-2-carboxamide (18.8 g:0.16 mole) in one liter of dried tetrahydrofuran was slowly added lithium aluminum hydride (33.9 g:0.89 mole) with stirring under cooling on ice, followed by refluxing the mixture for 48 hours. After cooling, the reaction mixture was treated with water and tetrahydrofuran by usual manner to give oil.

This was distilled under reduced pressure to give 6.07 g of (S)-2-aminomethylpyrrolidine as colorless liquid. Yield: 37%, b.p. 80°–85° C. (20 mmHg). $[\alpha]_D^{20}$ +10.02° (H$_2$O).

(S)-2-aminomethylpyrrolidine was lead to (S)-1,1-cyclobutanedicarboxylate(2-aminomethylpyrrolidine)-platinum(II) (Compound 2) by the same manner as described in Example 1. m.p. 240°–255° C. (decomposition).

Analysis: Calcd. for C$_{11}$H$_{18}$N$_2$O$_4$Pt: C 30.20, H 4.15, N 6.40 (%). Found: C 30.14, H 4.12, N 6.33 (%).

IR spectrum: $\nu_{max}^{KBr}$ cm$^{-1}$: 3100, 3190 (>NH), 1590, 1635 (>C=O)

$[\alpha]_D^{20}$ +39.17° (H$_2$O).

EXAMPLE 3

(R)-proline was led to (R)-2-aminomethylpyrrolidine by the same manner as in Example 2. b.p. 79°–85° C. (20 mmHg) $[\alpha]_D^{20} -8.67°$ (H$_2$O).

(R)-2-aminomethylpyrrolidine was further lead to (R)-1,1-cyclobutanedicarboxylate(2-aminomethylpyrrolidine)platinum(II) (Compound 3) by the same manner as described in Example 1. m.p. 248°–257° C. (decomposition).

Analysis: Calcd. for $C_{11}H_{18}N_2O_4Pt$: C 30.20, H 4.15, N 6.40 (%). Found, C 30.08, H 4.09, N 6.37 (%).

IR spectrum: $\nu_{max}^{KBr}$ cm$^{-1}$: 3100, 3190 (>NH), 1590, 1635 (>C=O).

$[\alpha]_D^{20} -40.10°$ (H$_2$O).

EXAMPLES 4–18

By the method described in Example 1, various compounds (Compounds Nos. 4–18) shown in Table 1 were prepared.

TABLE 1

$$\begin{array}{c} R_1 \; R_2 \\ CH-NH \\ (CH_2)_m \\ A \end{array} \underset{(R_3)_l}{\overset{(OH)_n}{\underset{(OH)_n}{Pt}}} \overset{X}{\underset{Y}{\phantom{Pt}}} \quad \begin{array}{c} (R_3)_l \\ N \\ A \end{array} CH-R_4$$

| Ex. No. | R₁ | R₂ | m | n | X / Y | $\overset{(R_3)_l}{\underset{CH-R_4}{N}}$ | molecular formula | m.p. (°C.) | elemental analysis cal'd (%) / found (%) C H N | IR $\nu_{max}^{KBr}$ cm⁻¹ |
|---|---|---|---|---|---|---|---|---|---|---|
| 4 | CH₃ | H | 0 | 0 | cyclobutane-1,1-dicarboxylate | NH-pyrrolidine (CH) | C₁₂H₂₀N₂O₄Pt | 253–257* | 31.92 4.46 6.20 / 31.72 4.48 6.16 | 3140, 3060 (NH), 1630, 1600 (C=O) |
| 5 | H | CH₃ | 0 | 0 | cyclobutane-1,1-dicarboxylate | NH-pyrrolidine (CH) | C₁₂H₂₀N₂O₄Pt | 272–277* | 31.92 4.46 6.20 / 31.87 4.40 6.19 | 3140 (NH), 1610, 1660 (C=O) |
| 6 | H | CH₂CH₃ | 0 | 0 | cyclobutane-1,1-dicarboxylate | NH-pyrrolidine (CH) | C₁₃H₂₂N₂O₄Pt | 270–277* | 33.54 4.76 6.02 / 33.49 4.56 6.05 | 3140 (NH), 1610, 1660 (C=O) |
| 7 | H | H | 0 | 0 | cyclobutane-1,1-dicarboxylate | N-CH₃ pyrrolidine (CH) | C₁₂H₂₀N₂O₄Pt | 234–237 | 31.92 4.46 6.20 / 31.65 4.50 6.25 | 3150, 3070 (NH), 1630, 1595 (C=O) |

TABLE 1-continued $$\begin{array}{c} R_1 \quad R_2 \\ | \quad | \\ CH-NH \\ | \\ (CH_2)_m \end{array} \underset{(OH)_n}{\overset{(OH)_n}{\underset{Pt}{\bigg|}}} \underset{Y}{\overset{X}{\bigg|}} \underset{CH-R_4}{\overset{(R_3)_l}{\underset{A}{\bigg\langle}}}$$

| Ex. No. | $R_1$ | $R_2$ | m | n | $\begin{array}{c}X\\Y\end{array}$ | $\underset{A}{\overset{N}{\bigg\langle}}\underset{CH-R_4}{\overset{(R_3)_l}{\bigg|}}$ | molecular formula | m.p. (°C.) | elemental analysis cal'd (%) C H N found (%) | IR $\nu_{max}^{KBr}$ cm$^{-1}$ |
|---|---|---|---|---|---|---|---|---|---|---|
| 8 | H | CH$_3$ | 0 | 0 | cyclobutane-1,1-dicarboxylate | N—CH$_3$ pyrrolidine | C$_{13}$H$_{22}$N$_2$O$_4$Pt | 260–263* | 33.54 4.76 6.02<br>33.51 4.77 6.13 | 3110 (>NH),<br>1625, 1655 (>C=O) |
| 9 | H | H | 0 | 0 | cyclobutane-1,1-dicarboxylate | N—CH$_2$CH$_3$ pyrrolidine | C$_{13}$H$_{22}$N$_2$O$_4$Pt | 264–274* | 33.54 4.76 6.02<br>33.47 4.62 5.92 | 3150, 3080 (>NH),<br>1620 (>C=O) |
| 10 | H | H | 0 | 0 | cyclobutane-1,1-dicarboxylate | NH pyrrolidine | C$_{10}$H$_{16}$N$_2$O$_4$Pt | 220–245* | 28.36 3.81 6.62<br>28.33 3.77 6.59 | 3170, 3100 (>NH),<br>1640, 1600 (>C=O) |
| 11 | H | H | 0 | 0 | oxalate | NH pyrrolidine | C$_7$H$_{12}$N$_2$O$_4$Pt | 271–275* | 21.93 3.15 7.31<br>21.73 3.15 7.51 | 3120 (>NH),<br>1690, 1665, 1635,<br>1600 (>C=O) |

TABLE 1-continued

| Ex. No. | R₁ | R₂ | m | n | X/Y | ![structure] | molecular formula | m.p. (°C.) | elemental analysis cal'd (%) / found (%) C H N | IR $\nu_{max}^{KBr}$ cm⁻¹ |
|---|---|---|---|---|---|---|---|---|---|---|
| 12 | CH₃ | H | 0 | 0 | O–C=O / O–C=O | NH (cyclopentyl) | C₈H₁₄N₂O₄Pt | 263–270* | 24.17 3.55 7.05 / 23.92 3.65 7.04 | 3120 (NH), 1690, 1660, 1630, 1605 (C=O) |
| 13 | H | CH₃ | 0 | 0 | O–C=O / O–C=O | NH (cyclopentyl) | C₈H₁₄N₂O₄Pt | 277–281* | 24.17 3.55 7.05 / 24.11 3.53 7.01 | 3120 (NH), 1638, 1662, 1691 (C=O) |
| 14 | H | CH₂CH₃ | 0 | 0 | O–C=O / O–C=O | NH (cyclopentyl) | C₉H₁₆N₂O₄Pt | 265–270* | 26.27 3.92 6.81 / 26.21 3.85 6.63 | 3120 (NH), 1660, 1690 (C=O) |
| 15 | H | CH₃ | 0 | 0 | O–C=O / O–C=O | N–CH₃ (cyclopentyl) | C₉H₁₆N₂O₄Pt | 259–268* | 26.27 3.92 6.81 / 26.22 3.89 6.75 | 3140 (NH), 1670, 1690 (C=O) |

TABLE 1-continued

| Ex. No. | R₁ | R₂ | m | n | X Y | (R₃)ₗ CH—R₄ N A | molecular formula | m.p. (°C.) | elemental analysis cal'd (%) found (%) C H N | IR ν$_{max}^{KBr}$ cm⁻¹ |
|---|---|---|---|---|---|---|---|---|---|---|
| 16 | H | H | 1 | 0 | O—C=O, O—C=O | N—CH₃ | C₈H₁₄N₂O₄Pt | 205–215* | 24.17 3.55 7.05<br>24.11 3.47 7.13 | 3135, 3210 (NH), 1655, 1698 (C=O) |
| 17 | H | H | 0 | 0 | O—C=O, O—C=O | N—CH₂CH₃ | C₉H₁₆N₂O₄Pt | 264–269* | 26.27 3.92 6.81<br>26.18 3.83 6.57 | 3080, 3155 (NH), 1650, 1670, 1695 (C=O) |
| 18 | H | H | 0 | 0 | O—C=O, O—C=O | N—CH₃<br>CH₃ | C₉H₁₆N₂O₄Pt | 275–285* | 26.27 3.92 6.81<br>26.30 3.86 6.55 | 3250, 3220, 3140 (NH), 1700, 1680, 1660, 1615 (C=O) |

*melting point with decomposition

EXAMPLE 19

To a solution of platinum(II) potassium chloride (4.15 g:0.01 mole) in 60 ml of water was added a solution of 2-aminomethylazetidine (0.86 g:0.01 mole) in 10 ml of water, and the mixture was stirred at room temperature for 4 hours. The resulting solid was collected by filtration, washed with water and dried at 60° C. under reduced pressure for 3 hours to give 2.64 g of dichloro(2-aminomethylazetidine)platinum(II) as white solid. Yield: 75%, m.p. 215°–235° C. (decomposition).

To the suspension of the above product (1.76 g:0.005 mole) in 3 ml of water was added 18 ml of 31% aqueous hydrogen peroxide with stirring at room temperature. The reaction mixture was subjected to reaction at room temperature for 30 minutes and then at 80° C. for 1 hour. After cooling, the resulting solid was collected by filtration, washed with water and dried at 60° C. under reduced pressure for 3 hours to give 1.16 g of cis-dichloro-trans-dihydroxy(2-aminomethylazetidine)-platinum(IV) (Compound 19) as light brown solid. Yield: 60%, m.p. 200°–200° C. (decomposition).

Analysis: Calcd. for $C_4H_{12}Cl_2N_2O_2Pt$: C 12.44, H 3.13, N 7.25 (%). Found: C 12.61, H 3.16, N 7.13 (%).

2-Aminomethylazetidine used in Example 19 as a starting compound was prepared by reducing azetidine-2-carboxyamide in tetrahydrofuran with lithium aluminum hydride.

EXAMPLES 20–27

By the method as in Example 19, compounds shown in Table 2 as Compounds 20–27 were preared.

TABLE 2

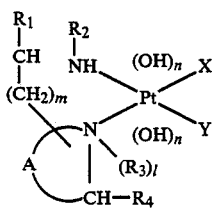

| Ex. No. | $R_1$ | $R_2$ | m | n | X/Y | A-ring | molecular formula | m.p. (°C.) | elemental analysis cal'd (%) / found (%) C H N | IR $\nu_{max}^{KBr}$ cm$^{-1}$ |
|---|---|---|---|---|---|---|---|---|---|---|
| 20 | H | H | 0 | 1 | Cl, Cl | NH | $C_5H_{14}Cl_2N_2O_2Pt$ | 220–230* | 15.00 3.53 7.00 / 15.19 3.37 6.90 | 540 (Pt—O) |
| 21 | $CH_3$ | H | 0 | 1 | Cl, Cl | NH | $C_6H_{16}Cl_2N_2O_2Pt$ | >300 | 17.39 3.89 6.76 / 17.27 3.78 6.68 | 545 (Pt—O) |
| 22 | H | $CH_3$ | 0 | 1 | Cl, Cl | NH | $C_6H_{16}Cl_2N_2O_2Pt$ | 200–205* | 17.39 3.89 6.76 / 17.22 3.84 6.51 | 540 (Pt—O) |
| 23 | H | H | 0 | 1 | Cl, Cl | N—$CH_3$ | $C_6H_{16}C_2N_2O_2Pt$ | 225–232* | 17.39 3.89 6.76 / 17.09 3.81 6.59 | 540 (Pt—O) |
| 24 | H | H | 0 | 1 | Cl, Cl | N—$CH_2CH_3$ | $C_7H_{18}Cl_2N_2O_2Pt$ | 183–185* | 19.63 4.24 6.54 / 19.70 4.16 6.51 | 530 (Pt—O) |
| 25 | H | H | 0 | 1 | Cl, Cl | N—$CH_3$, $CH_3$ | $C_7H_{18}Cl_2N_2O_2Pt$ | 199–201* | 19.63 4.24 6.54 / 19.60 4.17 6.25 | 535 (Pt—O) |
| 26 | H | H | 1 | 1 | Cl, Cl | N | $C_6H_{16}Cl_2N_2O_2Pt$ | 190–195* | 17.39 3.89 6.76 / 17.17 3.95 6.65 | 545 (Pt—O) |

TABLE 2-continued

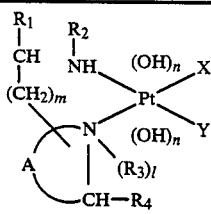

| Ex. No. | R₁ | R₂ | m | n | X Y | A⟨N(R₃)ₗ / CH—R₄⟩ | molecular formula | m.p. (°C.) | elemental analysis cal'd (%) / found (%) C H N | IR $\nu_{max}^{KBr}$ cm⁻¹ |
|---|---|---|---|---|---|---|---|---|---|---|
| 27 | H | H | 0 | 1 | Cl / Cl | NH | C₃H₁₀Cl₂N₂O₂Pt | 220–240* | 9.68 2.71 7.53 / 9.63 2.71 2.42 | 540 (Pt—O) |

*melting point with decomposition

EXPERIMENT 1

Test of in vivo antitumor activity against Colon 26 carcinoma

A small piece of Colon 26 tumor (1–2 mm³) was subcutaneously implanted in a lateral region of abdomen of a CDF₁/Crj strain male mouse (6 weeks old). Four days after the implantation, mice with the almost same size of tumor were divided into groups of 5–6 members each, and each mouse was intraperitoneally administered the test compound. Ten days after the administration, each of the mice was sacrificed, and the tumor was weighed to calculate the growth inhibitory ratio (GIR) by the following equation:

$$GIR\ (\%) = \frac{C - T}{C} \times 100$$

wherein C and T represent the mean weights of tumor of the control group and the treated group, respectively.

The results are shown in Table 3 below. Cisplatin (CDDP) which is a known compound was used as a comparison.

TABLE 3

| Antitumor Activity against Colon 26 Carcinoma | | |
|---|---|---|
| Compound No. | Dose (mg/kg) | GIR (%) |
| 1 | 40 | 79 |
|  | 60 | 87 |
|  | 80 | 98 |
|  | 120 | 97 |
|  | 160 | died |
| 2 | 40 | 73 |
|  | 60 | 88 |
|  | 80 | 94 |
|  | 120 | 98 |
|  | 160 | died |
| 3 | 40 | 70 |
|  | 60 | 85 |
|  | 80 | 90 |
|  | 120 | 95 |
|  | 160 | died |
| 10 | 40 | 80 |
|  | 60 | 88 |
|  | 80 | 98 |
|  | 120 | 98 |
|  | 160 | 99 |
| 19 | 40 | 60 |
|  | 60 | 77 |
|  | 80 | 85 |
|  | 120 | 92 |

TABLE 3-continued

| Antitumor Activity against Colon 26 Carcinoma | | |
|---|---|---|
| Compound No. | Dose (mg/kg) | GIR (%) |
|  | 160 | 95 |
| 20 | 40 | 70 |
|  | 60 | 76 |
|  | 80 | 88 |
|  | 120 | 91 |
|  | 160 | died |
| 26 | 40 | 56 |
|  | 60 | 68 |
|  | 80 | 71 |
|  | 120 | 83 |
|  | 160 | 86 |
| 27 | 40 | 31 |
|  | 60 | 58 |
|  | 80 | 63 |
|  | 120 | 75 |
|  | 160 | 88 |
| CDDP | 4 | 26 |
|  | 6 | 51 |
|  | 8 | 62 |
|  | 12 | 79 |
|  | 16 | died |

EXPERIMENT 2

Tests of in vivo antitumor activity against Colon 26 carcinoma

A small piece of Colon 26 tumor (1–2 mm³) was subcutaneously implanted in a lateral region of abdomen of a CDF₁/Crj strain male mouse (7 weeks old). Four days after the implantation, mice with the almost same size of tumor were divided into groups of 5–6 members each, and each mouse was intraperitoneally administered the test compound on day 4, 6, and 8 after implantation in a dose of 40 mg/kg one day. Fourteen days after the implantation, each mouse was sacrificed, and the tumor thereof was weighed to calculate the GIR (%) by the following equation.

$$GIR\ (\%) = \frac{C - T}{C} \times 100$$

where C and T represent the mean weights of tumor of the control group and the group administered the test compound, respectively.

The results are shown in Table 4.

TABLE 4

Antitumor Activity against Colon 26 Carcinoma

| Compound No. | CIR (%) |
|---|---|
| 1 | 98 |
| 2 | 99 |
| 3 | 95 |
| 10 | 99 |
| 20 | 82 |
| 21 | 91 |
| 23 | 87 |
| 24 | 90 |
| 25 | 85 |
| 26 | 85 |

EXPERIMENT 3

Comparison of in vitro binding property of the test compound relative to the plasma proteins A solution of the test compound was added to plasma obtained from SD strain rat at a ratio of 1:19 by volume which corresponded to 5 μg/ml of Pt. The mixture was incubated at 37° C. under dark. At a predetermined time, the mixture was sampled, and filtered with a molecular sieve membrane (manufactured by Amico Centriflow PMS) under centrifugation. The Pt content in the filtrate unbound Pt was assayed by an atomic absorption spectrophotometry.

The results are shown in Table 5.

TABLE 5

Percent binding to plasma proteins

| Compound No. | Incubation Time (hr) | | | |
|---|---|---|---|---|
| | 1 | 4 | 8 | 24 |
| 1 | 2 | 9 | 14 | 38 |
| 20 | 9 | 7 | 11 | 15 |
| 26 | 12 | 10 | 3 | 14 |
| CDDP | 16 | 62 | 86 | 93 |

EXPERIMENT 4

Test on side-effects $BDF_1$/Crj strain male mice (6 weeks old) were intraperitoneally administered the test compound, and 1, 3 and 5 days after the administration, 3 mice were saceificed to determine the body weight and the level of urea nitrogen in blood (abbreviated as BUN).

The results are shown in Table 6 below.

TABLE 6

Body weight and BUN

| Items for measurement | Dose of the Compound (mg/kg) | Days after Administration | | |
|---|---|---|---|---|
| | | 1 | 3 | 5 |
| Body weight (g) (mean SD) | Control (—) | 23.6 ± 1.0 | 23.7 ± 1.4 | 24.4 ± 1.4 |
| | Compound No. 2 (60) | 23.1 ± 1.4 | 19.9 ± 1.6** | 17.9 ± 1.1** |
| | Compound No. 3 (60) | 23.4 ± 1.5 | 20.1 ± 1.2** | 17.5 ± 0.7** |
| | CDDP (12) | 24.6 ± 1.1 | 22.55 ± 1.1 | 19.0 ± 1.5** |
| BUN (mg/dl) (mean SD) | Control (—) | | 17.10 ± 4.35 | |
| | Compound No. 2 (60) | 20.0 ± 2.6 | 17.7 ± 3.1 | 15.4 ± 5.5 |
| | Compound No. 3 (60) | 18.3 ± 3.1 | 13.8 ± 1.8 | 13.8 ± 7.6 |
| | CDDP (12) | 23.3 ± 4.7* | 38.5 ± 28.9 | 65.2 ± 31.5** |

*$P < 0.05$
**$P < 0.01$

FORMULATION OF PHARMACEUTICAL PREPARATION (a) Injection:

An aqueous solution of compound No. 1 prepared in the Example was charged in vials by aseptic manipulation so that each vial contains 50 mg of the compound. The content of each vial was dried and sterilized, and the vials were sealed. When used as an injection, 10 ml of physiological saline was added to the vial to make up the injection.

Alternately, when used as an intravenous drip infusion, the preparation was dissolved in a suitable fluid therapy such as a physiological saline or glucose-saline or the like.

(b) Tablet:

Compound No. 1: 50 g
Lactose: 96 g
Crystalline cellulose: 27 g
Corn starch: 5 g
Magnesium stearate: 2 g The above ingredients were intimately mixed and directly compressed by a tableting machine into tablets having a diameter of 8 mm and weighing 180 mg each.

From the results obtained by Experiments 1 and 2 (Tables 3 and 4), it can be seen that the compounds of this invention exhibited a stronger antitumor activity and are effective over a broader range of dose level in comparison with those of CDDP.

In addition, although it is generally considered that a platinum complex is binded with plasma proteins to form an inactive substance, the compound of this invention exhibits a significantly lower binding property with plasma proteins than that of CDDP. The compounds of this invention have reduced toxicity and high water-solubility, and are therefore useful as an antitumor medicine.

What is claimed is:

1. A platinum complex of the formula:

$$\begin{array}{c} CH_2-NH_2 \\ | \\ CH-NH \\ | \\ A-CH_2 \end{array} \diagdown Pt \diagup \begin{array}{c} (OH)_n \\ \diagdown X \\ (OH)_n \diagup Y \end{array}$$

wherein A is $-CH_2-$ or $-(CH_2)_2-$; X and Y are independently a Cl atom, or combined together to form $$\begin{array}{c} -O-C \overset{\displaystyle O}{\diagup} \\ -O-C \diagdown_O \end{array} \!\!\!\!\!\bowtie$$

and n is 0 or 1; provided that X and Y are combined together to form

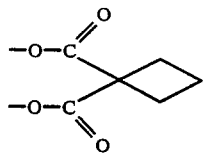

when n is 0, of X and Y are independently a Cl atom when n is 1.

2. 1,1-Cyclobutanedicarboxylate(2-aminomethylpyrrolidine)-platinum(II), according to claim 1.

3. 1,1-Cyclobutanedicarboxylate(2-aminomethylazetidine)platinum(II), according to claim 1.

4. cis-Dichloro-trans-dihydroxy(2-aminomethylpyrrolidine)platinum(IV), according to claim 1.

5. cis-Dichloro-trans-dihydroxy(2-aminomethylazetidine)platinum(IV), according to claim 1.

* * * * *